US006818763B2

(12) United States Patent
Vukovich et al.

(10) Patent No.: US 6,818,763 B2
(45) Date of Patent: Nov. 16, 2004

(54) PREPARATION OF METAL MESOPORPHYRIN HALIDE COMPOUNDS

(75) Inventors: Robert A. Vukovich, Holmdel, NJ (US); Benjamin Levinson, Montgomery, NJ (US); George S. Drummond, New York, NY (US); Robert Caroselli, East Brunswick, NJ (US); Kazimierz G. Antczak, Culver, IN (US); Christopher Boucher, Newmarket (CA); Richard Mortimer, Toronto (CA)

(73) Assignee: Wellspring Pharmaceutical Corporation, Neptune, NJ (US)

( * ) Notice: Subject to any disclaimer, the term of this patent is extended or adjusted under 35 U.S.C. 154(b) by 0 days.

(21) Appl. No.: 10/453,815

(22) Filed: Jun. 3, 2003

(65) Prior Publication Data

US 2003/0225264 A1 Dec. 4, 2003

Related U.S. Application Data

(60) Provisional application No. 60/385,498, filed on Jun. 4, 2002.

(51) Int. Cl.$^7$ ............................................. C07D 487/22
(52) U.S. Cl. ....................................... 540/145; 540/121
(58) Field of Search ................................ 540/145, 121

(56) References Cited

U.S. PATENT DOCUMENTS

| | | | |
|---|---|---|---|
| 4,657,902 A | 4/1987 | Kappas et al. ............... 514/185 |
| 4,684,637 A | 8/1987 | Kappas et al. ............... 514/185 |
| 4,692,440 A | 9/1987 | Kappas et al. ............... 514/185 |
| 4,782,049 A | 11/1988 | Kappas et al. ............... 514/185 |
| 4,861,876 A | 8/1989 | Kessel |
| 4,900,871 A | 2/1990 | Ellis, Jr. et al. |
| 5,192,757 A | 3/1993 | Johnson et al. |
| 5,371,199 A | 12/1994 | Therien et al. |
| 5,493,017 A | 2/1996 | Therien et al. |
| 5,817,830 A | 10/1998 | Therien et al. |
| 5,883,246 A | 3/1999 | Bruckner et al. |
| 5,886,173 A | 3/1999 | Hemmi et al. |
| 5,889,181 A | 3/1999 | Kudrevich et al. |
| 5,929,064 A | 7/1999 | Goel et al. |
| 5,955,603 A | 9/1999 | Therien et al. |
| 5,973,141 A | 10/1999 | Robinson et al. |
| 5,990,363 A | 11/1999 | Wijesekera et al. |
| 6,004,530 A | 12/1999 | Sagner et al. |
| 6,114,321 A | 9/2000 | Platzek et al. |
| 6,124,452 A | 9/2000 | DiMagno |
| 6,177,561 B1 | 1/2001 | Sinn et al. |
| 6,194,566 B1 | 2/2001 | Platzek et al. |
| 6,235,895 B1 | 5/2001 | McEwan et al. |
| 6,420,553 B1 | 7/2002 | Inoue et al. ................. 540/145 |
| 6,462,192 B2 | 10/2002 | Robinson et al. ........... 540/145 |

OTHER PUBLICATIONS

"Photophysical Properties of Sn–Porphyrins: Potential Clinical Implications", John K. Delaney et al., Pediatrics, vol. 81, No. 4, Apr. 1988, pp. 498–504.

"Stability–Indicating High–Performance Liquid Chromatographic Analysis of Tin Protoporphyrin and other Free Acid Metalloporphyrins", John Bauer et al., Journal of Chromatography, 445 (1988) 429–432.

John K. Delaney, BS, David Mauzerall, PhD, George S. Drummond, PhD, Attallah Kappas, MD; Photophysical Properties of Sn–Porphyrins: Potential Clinical Implications; Pediatrics vol. 81, No. 4, Apr., 1988; Rockefeller University Hospital, NY.

John Bauer, Cathie Linton, Barbara Norris; Stability–indicating high performance.

Liquid chromatographic analysis of tin protoporphyrin and other free acid metalloporphyrins; Journal of Chromatography 445, pp. 429–432, published 1988 in Amsterdam.

Primary Examiner—John M. Ford
(74) Attorney, Agent, or Firm—Lerner, David, Littenberg, Krumholz & Mentlik, LLP

(57) ABSTRACT

A method of preparing metal mesoporphyrin halide compounds is described. The metal mesoporphyrin halide compound may be formed by forming a novel mesoporphyrin IX intermediate compound and then converting the mesoporphyrin IX intermediate to the metal mesoporphyrin halide through metal insertion. The novel intermediate compound may be formed by a catalytic hydrogenation of hemin in acid and subsequent recovery.

33 Claims, 5 Drawing Sheets

$x = 0.5 - 2.5$

PREPARATION OF METAL MESOPORPHYRIN HALIDE COMPOUNDS

CROSS-REFERENCE TO RELATED APPLICATIONS

The present application claims priority from U.S. Provisional Application No. 60/385,498, filed on Jun. 04, 2002, the disclosures of which are hereby incorporated by reference herein.

BACKGROUND OF THE INVENTION

Field of the Invention

The present invention generally relates to metal mesoporphyrin halide compounds and processes for their preparation. More specifically, it relates to processes for making novel intermediate compounds which can be converted to such mesoporphyrin halide compounds.

Tin (IV) mesoporphyrin IX dichloride or stannsoporfin is a chemical compound having the structure indicated in FIG. 1. It has been proposed for use, for example, as medicament in the treatment of various diseases including, for example, psoriasis (U.S. Pat. No. 4,782,049 to Kappas et al.) and infant jaundice (for example, in U.S. Pat. Nos. 4,684,637, 4,657,902 and 4,692,440). Stannsoporfin is also known to inhibit heme metabolism in mammals, to control the rate of tryptophan metabolism in mammals, and to increase the rate at which heme is excreted by mammals (U.S. Pat. Nos. 4,657,902 and 4,692,400 both to Kappas et al.).

Processes for obtaining stannsoporfin are known in the art. Protoporphyrin IX iron (III) chloride or hemin, of the structural formula indicated in FIG. 2, is commonly used as starting material. The hemin is generally hydrogenated to form an intermediate mesoporphyrin IX dihydrochloride, which is subsequently subjected to tin insertion, yielding stannsoporfin.

One prior method for the preparation of the intermediate mesoporphyrin IX dihydrochloride has involved catalytic hydrogenation of hemin over Pd(0) in formic acid at elevated temperature. Column chromatography of the resulting intermediate obtained by such a method yields an intermediate mesoporphyrin IX dihydrochloride product that reportedly contains about 15% of an unidentified impurity. Another preparation method for this intermediate has been typically performed at lower temperatures with heating hemin in formic acid in the presence of palladium catalyst. This process is reported to reduce the amount of the unidentified impurity; however, the reaction is difficult to drive to completion without decomposition of the intermediate product.

The above referenced methods for the preparation of the mesoporphyrin IX intermediate are used to produce only small, gram scale quantities of the product, and the product further requires subsequent isolation and purification, generally by preparative or column chromatography. Additionally, those methods in which hydrogenation is carried out at lower temperatures yield incomplete reactions, and when higher temperatures are used, degradation of the intermediate product is observed. Consequently, the crude intermediate product requires purification. Furthermore, the above referenced procedures require exceedingly high solvent volumes, thus making the process unsuitable for industrial scale up, since isolation of mesoporphyrin IX dihydrochloride or its free base is performed using a filtration process. Such filtrations and subsequent washings of the products are time-consuming, making the large-scale isolations costly and difficult. Additionally, the limited stability of mesoporphyrin IX in hydrochloric acid at the elevated temperatures required to form the dihydrochloride also complicates the industrial scale up of this process.

The insertion of various metals into porphyrin rings, including the insertion of tin into mesoporphyrin IX, has been described by Fischer and Neumann (Ann. Chem. (1932), 494, 225). The reaction for the insertion of tin is performed in an acid, typically acetic acid, and further typically under reflux, using Sn (II) in the presence of an oxidant. A modified process is also described by Fuhrhop and Smith, as reported in "Porphyrins and Metalloporphyrins" p. 757, Elsvier, Amsterdam, 1975, to include sodium acetate, which buffers the solution and enhances deprotonation of the porphyrin. In most cases, the metal mesoporphyrin halide product crystallizes directly from the reaction mixture on cooling. Such crystallization may be enhanced by the addition of water or methanol.

SUMMARY OF THE INVENTION

It is an object of the present invention to provide a novel process for the preparation of metal mesoporphyrin halides that overcomes some of the difficulties of the processes known in the art.

It is a further object of the invention to provide a novel intermediate useful in the preparation of tin mesoporphyrin chloride and other metal mesoporphyrin halides.

It has now been discovered that, if the catalytic hydrogenation of hemin is conducted in formic acid, in two distinct states, each using different reaction conditions, a novel intermediate compound, a mesoporphyrin IX formate, is formed. This compound can be precipitated so that it can be isolated in a substantially pure, solid form. Then the substantially pure intermediate can be reacted to insert metals such as tin, and obtain metal mesoporphyrin halides with a high degree of purity, capable of further purification if necessary, by simple procedures capable of being conducted on an industrial scale.

Thus the invention provides, from a first aspect, a process of preparing a mesoporphyrin IX formate, which comprises subjecting hemin to catalytic hydrogenation in formic acid, said hydrogenation being conducted in two successive steps comprising:

the first step of subjecting a mixture of hemin and a hydrogenation catalyst in formic acid to hydrogen pressure of about 30–60 psi then raising the temperature to about 85–95° C., and maintaining the temperature within that range for a period of about 1–3 hours;

the second step of subjecting said mixture to further hydrogen pressure of about 30–60 psi at temperatures of about 45–50° C. for a period of about 3–6 hours; and recovering the mesoporphyrin IX formate from the reaction mixture by precipitation with an ether or other organic solvent.

Mesoporphyrin IX formate, which has the following structural chemical formula indicated in FIG. 3, is a novel chemical compound, and constitutes a second aspect of the present invention.

Alternatively and preferably, the reactor may be pressurized with $H_2$ gas prior to the heating step. Pressurizing the reactor with hydrogen prior to heating, in the first step of the process, reduces degradation, while exceeding the times and the temperatures set out above for the first step increases degradation. On the other hand, shorter reaction times and lower temperatures will lead to undesirable decreases in conversion, leading to low product yields.

The second step as defined above completes the conversion of the hemin (protoporphrin IX) to mesoporphyrin IX formate.

Isolation of the intermediate product as a formate provides a readily filterable intermediate, filtering and washing of which to obtain at least a substantially high purity intermediate product (about >97%) is a simple procedure. The purity of the intermediate is important in the manufacturing of the final product, whether stannsopofin or other metal mesoporphyrin halides, in that a higher purity intermediate produces a higher purity product.

A second process aspect of the present invention comprises a process of converting a mesoporphyrin IX formate, to a metal mesoporphyrin halide which comprises:

drying the mesoporphyrin IX formate;

subjecting the mesoporphyrin IX formate, to a chemical metal insertion process by reaction with a metal halide compound, under buffered, acidic reaction conditions and in the presence of an oxidant; and recovering the metal mesoporphyrin halide from the reaction mixture.

The invention provides, from a third aspect, a process of purification of a metal mesoporphyrin halide, which comprises the steps of:

(a) dissolving the metal mesoporphyrin halide in an aqueous basic solution to obtain a dissolved metal mesoporphyrin halide;

(b) treating said dissolved metal mesoporphyrin halide with charcoal to obtain a treated metal mesoporphyrin halide;

(c) adding said treated metal mesoporphyrin halide to a first aqueous acid solution to obtain a precipitated metal mesoporphyrin halide;

(d) triturating said precipitated metal mesoporphyrin halide in a second aqueous acid solution at elevated temperature to obtain a pharmaceutical grade pure (about or more than 97%) metal mesoporphyrin halide; and (e) drying the pharmaceutical grade pure metal mesoporphyrin halide.

A fourth aspect of the invention comprises a process of preparing a metal mesoporphyrin halide, which comprises subjecting hemin to a two step catalytic hydrogenation comprising:

the first step of subjecting a mixture of hemin and a hydrogenation catalyst in formic acid to hydrogen pressure of about 30–60 psi then raising the temperature to about 85–95° C., and maintaining the temperature within that range for a period of about 1–3 hours;

the second step of subjecting said mixture to further hydrogen pressure of about 30–60 psi at temperatures of about 45–50° C. for a period of about 3–6 hours;

recovering the mesoporphyrin IX formate from the reaction mixture by precipitation with an ether or other organic solvent;

drying the mesoporphyrin IX formate;

subjecting the mesoporphyrin IX formate, to a chemical metal insertion process by reaction with a metal halide compound, under buffered, acidic reaction conditions and in the presence of an oxidant; and recovering the metal mesoporphyrin halide from the reaction mixture.

In accordance with an embodiment of this fourth aspect, the process can further comprise the purification steps of:

(a) dissolving the metal mesoporphyrin halide in an aqueous basic solution to obtain a dissolved metal mesoporphyrin halide;

(b) treating said dissolved metal mesoporphyrin halide with charcoal to obtain a treated metal mesoporphyrin halide;

(c) adding said treated metal mesoporphyrin halide to a first aqueous acid solution to obtain a precipitated metal mesoporphyrin halide;

(d) triturating said precipitated metal mesoporphyrin halide in a second aqueous acid solution at elevated temperature to obtain a substantially pure (about or more than 95%) metal mesoporphyrin halide; and (e) drying said substantially pure metal mesoporphyrin halide.

In all the embodiments of the fourth process aspect according to the invention, steps (a) to (c) may be carried out at least twice prior to subjecting the precipitated metal mesoporphyrin halide to step (d).

DETAILED DESCRIPTION

Figure 1:
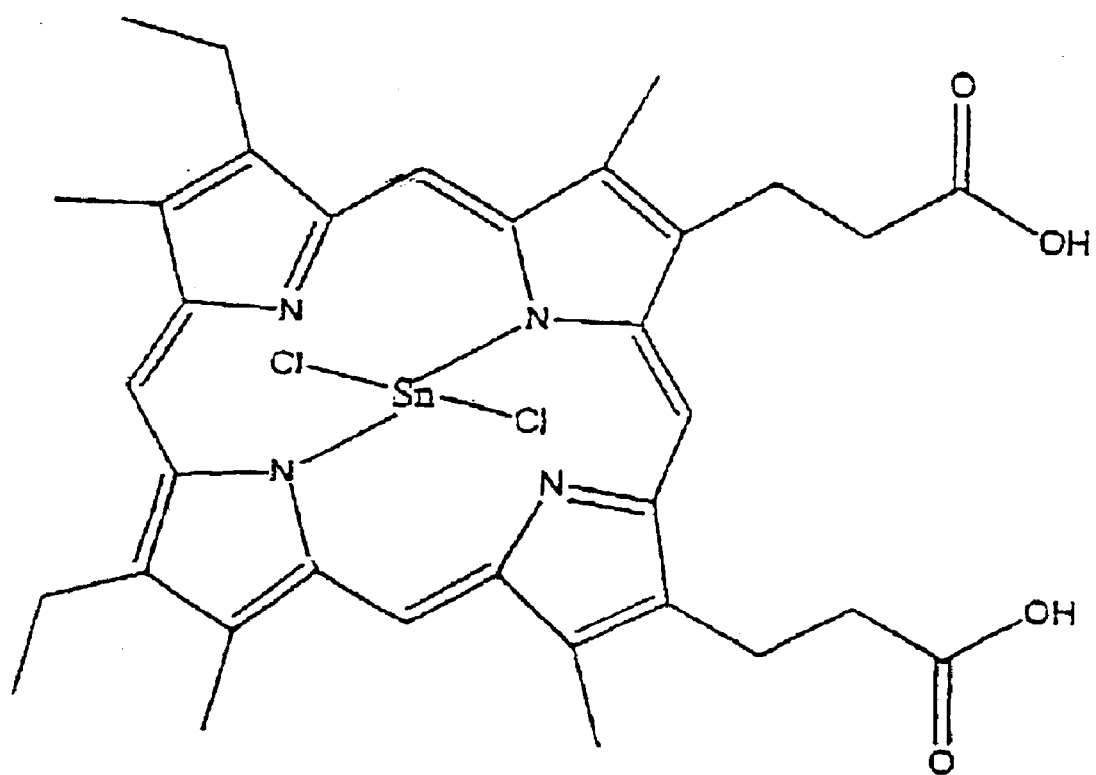
FIG. 1 illustrates the chemical structure of tin mesoporphyrin chloride (tin (IV) mesoporphyrin IX dichloride) or stannsoporfin.
Figure 2:
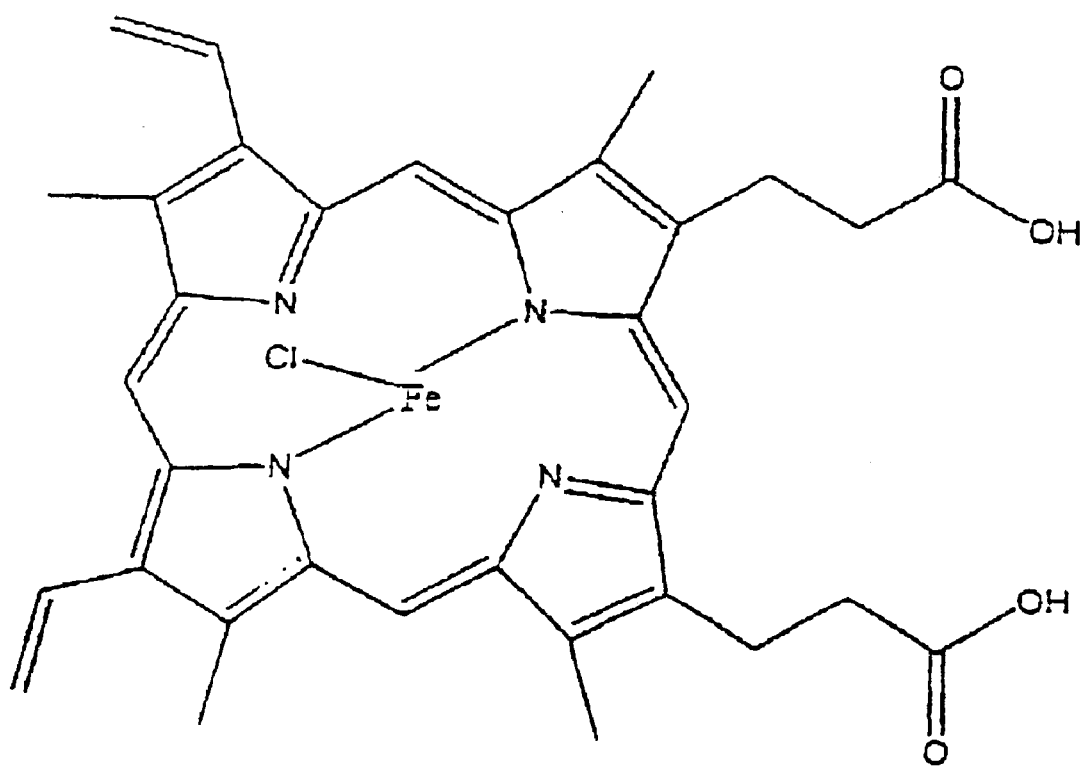
FIG. 2 illustrates the chemical structure of protoporphyrin IX iron (III) chloride or hemin.
Figure 3:
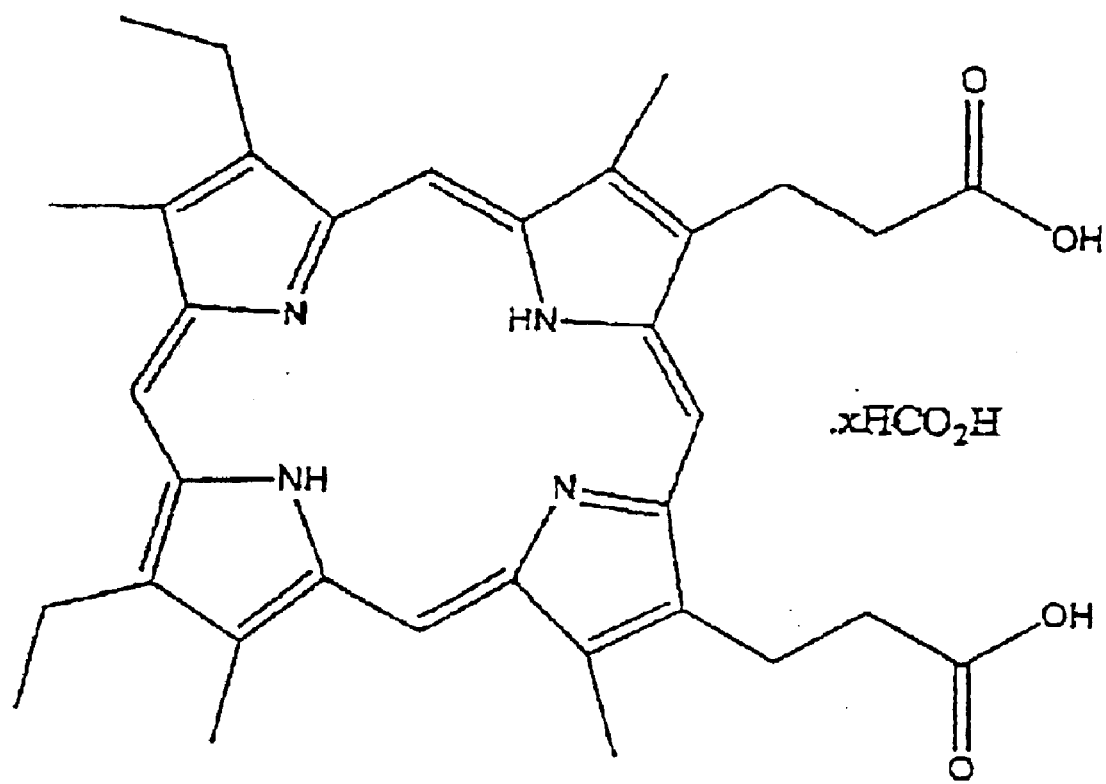
FIG. 3 illustrates the chemical structure of mesoporphyrin IX formate, a novel chemical compound, which constitutes a novel product of the present invention.
Figure 4:
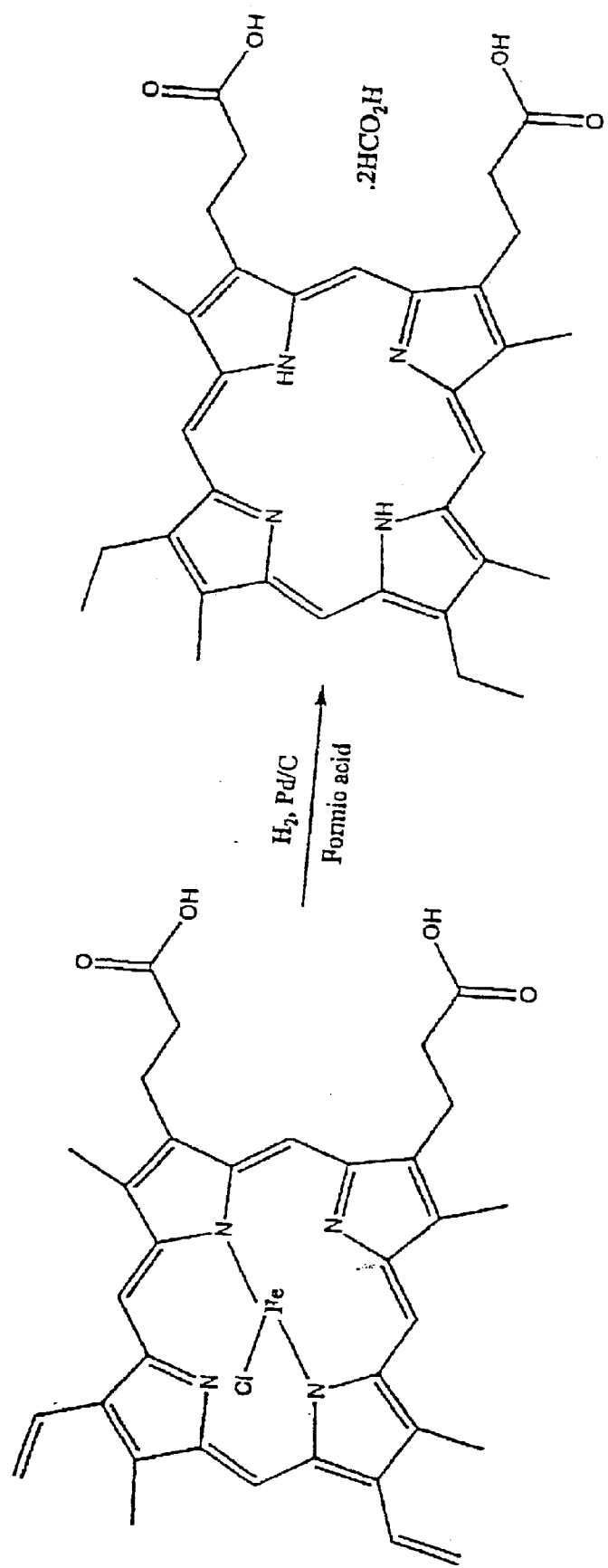
FIG. 4 illustrates the conversion of protoporphyrin IX iron (III) chloride (ferriporphyrin chloride or hemin) to mesoporphyrin IX formate, in accordance with an embodiment of the first aspect of the invention.

In the first aspect of an example of the invention, illustrated in accompanying FIG. 4, hemin is hydrogenated in formic acid, over an appropriate metal catalyst such as, for example, palladium, platinum or nickel, among others, under a hydrogen atmosphere, at elevated temperatures. Preferred embodiments of the invention involve the use of palladium on carbon as metal catalyst. In the first stage of hydrogenation, the temperature of hydrogenation is held at about 85–95° C. for a period of about 1–3 hours. Most preferred conditions are a temperature of about 90° C. and a time of about 1 hour.

In the second stage of hydrogenation, the reaction mixture is cooled to about 45–50 ° C. and hydrogenated for a further period of time of about 3–6 hours, in order to convert substantially all hemin (protoporphyrin IX iron (III) chloride) to mesoporphyrin IX formate. This second stage is also conducted in formic acid. The same catalyst may be used as in the first aspect above, so that the two stages of the process may be conducted in the same reactor. Optionally, a further charge of hydrogen may be supplied to the reactor prior to commencing the second stage. The second hydrogenation stage increases the yield of the mesoporphyrin IX formate, while reducing the amount of impurities in the final metal mesoporphyrin halide.

In contrast to previously described methods, the mesoporphyrin IX intermediate compound in the present invention is not isolated as a dihydrochloride, but rather as a formate salt.

The mesoporphyrin IX formate may be isolated from the formic acid solution by the addition of a solvent such as an ether or other organic solvent, leading directly to the mesoporphyrin IX formate intermediate, which is further subjected to drying. Ethers such as, for example, methyl tert-butyl ether, diethyl ether or di-isopropyl ether, among others, may be used. Preferred embodiments of the invention involve methyl tert-butyl ether.

The amounts of solvent used in the process according to the invention are much lower than those used in the referenced processes; such smaller volumes allow for less filter time. Ratios of amount of hemin to amount of solvent of about 1:10 to about 1:20 may be used. In addition, the filtration and washings of the mesoporphyrin IX formate are rapid. After drying, the crude intermediate formate is obtained, in high yields (about 80–95%) and its purity, established by HPLC, is about or above 97%. The intermediate formate obtained in accordance with the process of the invention is of quality equal to or better than that of the intermediate mesoporphyrin IX dihydrochloride produced in the process described in the art, after purification by preparative chromatography.

The insertion of metal into mesoporphyrin IX formate to obtain metal mesoporphyrin halide is described below with specific reference to tin, to prepare stannsoporfin, a known pharmaceutical and a specific preferred embodiment of the invention. It is not intended that the scope of the invention should be limited thereto, but is generally applicable to preparation of mesoporphyrin halides, for example, but not limited to, mesoporphyrin chlorides, of other metals such as, for example, iron, zinc, chromium, manganese, copper, nickel, magnesium, cobalt, platinum, gold, silver, arsenic, antimony, cadmium, gallium, germanium and palladium, among others.

Preparation of mesoporphrin halides of these other metals simply entails a substitution of a halide such as chloride, bromide or iodide of the chosen metal in place of stannous chloride in the process described, in substantially equivalent amounts.

Figure 5:
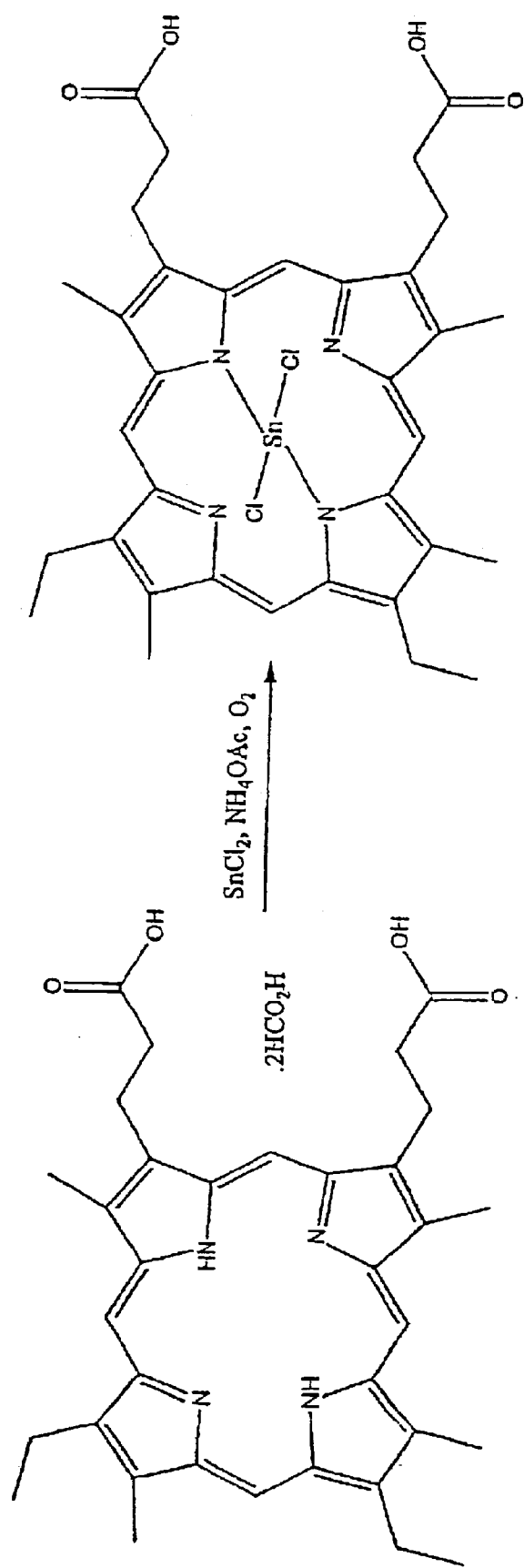
FIG. 5 illustrates the conversion of mesoporphyrin IX formate to tin mesoporphyrin chloride (tin (IV) mesoporphyrin IX dichloride) or stannsoporfin, in accordance with an embodiment of the second aspect of the invention.

The second stage of the process according to the invention is illustrated in FIG. 5. Mesoporphyrin IX formate is subjected to heating with a tin (II) carrier in acetic acid, buffered with an acetate ion, in the presence of an oxidant, at reflux. Tin (II) carriers such as tin (II) halides or tin (II) acetate can be used. Suitable acetate counter ions include ammonium, sodium or potassium ions. Oxidants such as oxygen from air or in pure form as well as hydrogen peroxide can also be used. In one exemplary embodiment of this second stage, mesoporphyrin IX formate is subjected to heating with tin (II) chloride in acetic acid, buffered with ammonium acetate, and the reaction is conducted in the presence of air, at reflux. Tin mesoporphyrin chloride is isolated from the reaction mixture by the addition of water, followed by filtration. Prior to drying at about 90–100° C., the cake is triturated into hot, dilute hydrochloric acid, preferably of concentration of about 0.1N–6N, at an elevated temperature, of about 90–100° C. The crude, substantially pure tin mesoporphyrin chloride (crude tin (IV) mesoporphyrin IX dichloride) is obtained with a yield of about 75–95% and a purity of about 95%, as judged by HPLC analysis.

The tin mesoporphyrin chloride so obtained may be further purified by dissolving the product in an aqueous inorganic base solution, preferably dilute ammonium hydroxide, followed by treatment with charcoal. The product is then re-precipitated by addition to an acid solution, such as acetic acid, hydrochloric acid or a mixture thereof. The above dissolving, charcoal treatment and re-precipitation steps may be repeated a number of times, typically about 1–3 times in order to ensure the desired purity. Prior to drying, the cake is triturated in hot, dilute hydrochloric acid of a concentration of about 0.1N–6N, at an elevated temperature of about 90–100° C., in order to remove any residual ammonium salts. The tin mesoporphyrin chloride product (tin (IV) mesoporphyrin IX dichloride or stannsoporfin) is obtained in a yield of about 50–70%, with an HPLC purity of about or greater than 97%.

The invention may also be performed to produce substantially pure or pharmaceutical quality tin mesoporphyrin chloride (tin (IV) mesoporphyrin IX dichloride or stannsoporfin) in large scale quantities, such as quantities exceeding about 0.1 kg through and including multiple kilogram amounts, by slight modifications of the above procedure, such as increased reaction or drying times as appropriate based upon the increase in scale of the starting reactants. Temperature and pressure times likewise can be modified as needed within the scope of this invention. The tin mesoporphyrin chloride product (tin (IV) mesoporphyrin IX dichloride or stannsopofrin) is obtained in the large-scale production process in a yield of about 60–90%, with an HPLC purity of about 97%.

The invention will be further described, for illustrative purposes, with reference to the following specific experimental examples.

EXAMPLE 1

Preparation of mesoporphyrin IX formate—A 2000 ml hydrogenation vessel was charged with 40.0 g hemin, 4.0 g 5% Pd/C (50% water by weight), and 800 ml 96% formic acid. Since hemin and mesoporphyrin IX formate as well as all reaction intermediates are reportedly light sensitive materials, care was taken throughout this entire procedure to minimize the exposure of the reaction to visible or ultraviolet light.

The vessel was flushed with a nitrogen flow for 10 minutes. With vigorous stirring, it was then pressurized to 50 psi with hydrogen for ten minutes; then depressurized, and the cycle repeated. The vessel was further pressurized to 50 psi with hydrogen and the temperature was raised to 90° C. over approximately 20 minutes.

The hydrogenation reaction was maintained at 90° C. and 45–55 psi for 1–1.5 hours. The reaction mixture was not stable for extended periods of time at 90° C. The time at this temperature was sufficient to dissolve all hemin and convert the majority of this material to the intermediate and final product, mesoporphyrin IX formate. The reaction was cooled to 50° C./50 psi over 20 minutes. This pressure and temperature were maintained for 3 hours. The reaction mixture was shown to be stable at this temperature for up to 18 hours. The reaction was cooled to 20–25° C., de-pressurized, and flushed with nitrogen.

The catalyst was removed by filtration through a bed of 20 g celite. The filter cake was rinsed with 3×50 ml formic acid and the filtrate was charged to a 2000 ml three-necked, round-bottom flask equipped with a magnetic stirbar, thermometer, and distillation bridge. The formic acid solvent was distilled off under aspirator vacuum to a residual volume of 200 ml. The distillation bridge was replaced with an addition funnel. With moderate agitation, 800 ml methyl tert-butyl ether was added dropwise over 30–60 minutes. The resultant suspension was agitated at 20–25° C. for 60 minutes prior to cooling to −20 to −25° C. for 1 to 2 hours. The suspension was filtered under reduced pressure. The filtercase was rinsed with 100 ml filtrate, followed by 2×50 ml methyl tert-butyl ether and dried under high vacuum at 40–60° C. for 24 hours. About 30–38 g of mesoporphyrin IX formate were obtained (yield of 75–95%).

EXAMPLE 2

Preparation of Substantially Pure Tin Mesoporphyrin Chloride (tin (IV) mesoporphyrin IX dichloride or stannsoporfin). A dark 1000 ml three-necked, round-bottom flask equipped with a mechanical stirrer, condenser, bubbler, and an aeration tube was charged with 30.0 g mesoporphyrin IX formate, 34.5 g tin (II) chloride, 7.1 g ammonium acetate, and 600 ml acetic acid. The suspension was stirred at 20–25° C. for 30 minutes. Mesoporphyrin IX formate and tin mesoporphyrin as well as all reaction intermediates are reportedly light sensitive materials therefore care was taken throughout this entire procedure to minimize the exposure of the reaction to light.

The reaction was warmed to reflux, with aeration, for 3 to 4 hours. The reaction was shown to be stable at 110–115° C. for up to 48 hours. Once complete, the reaction mixture was cooled to 60–70° C. and 300 ml water was added while cooling to 20–25° C. over 60 minutes. The suspension was filtered under reduced pressure. The filtercake was rinsed with 2×60 ml water. A dark, 1000 ml, three-neck, round-bottom, flask equipped with a stir bar, thermometer, condenser, and nitrogen purge was charged with the wetcake from the above step, and 500 ml 1N HCl. The resultant suspension was warmed to 90° C. for 1 hour. The suspension was filtered under reduced pressure. The filtercake was rinsed with 2×50 ml 0.1N HCl and dried under high vacuum at 80–90° C. for 24 hours. About 25 to 28 g of crude, substantially pure (about or exceeding 95% purity) tin mesoporphyrin chloride (tin (IV) mesoporphyrin IX dichloride or stannsoporfin) was obtained for a yield of about 83–93%.

EXAMPLE 3

Further Purification of crude, substantially pure tin (IV) mesoporphyrin chloride (tin (IV) mesoporphyrin IX dichloride or stannsoporfin). A darkened, 250 ml, one-neck, round-bottom flask equipped with a magnetic stirbar and nitrogen purge was charged with: 10.0 g tin (IV) mesoporphyrin chloride (tin (IV) mesoporphyrin IX dichloride), 125 ml water, and 4 ml 28% ammonium hydroxide, a sufficient amount of ammonium hydroxide to adjust the pH to 9.0–10.0. The suspension was stirred at 20–25° C. for 20–30 minutes to effect dissolution. As tin (IV) mesoporphyrin is light sensitive, dark conditions were maintained throughout this reaction sequence.

The flask was charged with 0.5 g Darco KB, and a 1.5 g Celite. The dark suspension was stirred at 20–25° C. for 1 hour. The suspension was filtered under reduced pressure through a bed of celite using a 5.5 cm Buchner funnel. The flask and filtercake were rinsed with 2×10 ml water. A dark, 1 L, one-neck, round-bottom flask equipped with a magnetic stirbar, addition funnel and nitrogen purge was charged with 375 ml acetic acid, and 10 ml 37% hydrochloric acid. The filtrate from the celite filtration step was charged to the addition funnel and added dropwise to the stirring acid solution over 30–45 minutes. The suspension was stirred at 20–25° C. for 1–2 hours; then filtered under reduced pressure using a 7 cm Buchner funnel. The filtercase was rinsed with 2×10 ml water.

A darkened, 250 ml, one-neck, round-bottom flask equipped with a magnetic stirbar and nitrogen purge was charged with the tin mesoporphyrin wet cake from the above step, 125 ml 27% ammonium hydroxide, and 4 ml water. The suspension was stirred at 20–25° C. for 20–30 minutes to effect dissolution and the pH adjusted to about 9.0–10.0 with additional ammonium hydroxide. The flask was charged with 0.5 g Darco KB, and 1.5 g Celite. The dark suspension was stirred at 20–25° C. for 1 hour. The suspension was filtered under reduced pressure through a bed of celite using a 5.5 cm Buchner funnel. The flask and filtercake were rinsed with 2×10 ml water.

A dark 1L one-neck, round-bottom flask equipped with a magnetic stirbar, addition funnel and nitrogen purge was charged with 375 ml acetic acid, and 10 ml 37% hydrochloric acid. Once the addition was complete, the pH was adjusted to about less than or equal to 1 by the addition of 37% hydrochloric acid. The filtrate from the above celite filtration step was charged to the addition funnel and added dropwise to the stirring acid solution over 30–45 minutes. Once the addition was complete, the pH was adjusted to about less than or equal to 1 by the addition of hydrochloric acid. The suspension was stirred at 20–25° C. for 1–2 hours; then filtered under reduced pressure using a 7 cm Buchner funnel. The filtercake was rinsed with 2×10 ml water.

A darkened, 250 ml, one-neck, round-bottom flask equipped with a magnetic stirbar and nitrogen purge was charged with tin mesoporphyrin wet cake from the above step, 125 ml water, and 4 ml 27% ammonium hydroxide. The suspension was stirred at 20–25° C. for 20–30 minutes to effect dissolution. The pH was adjusted to about 9.0–10.0 with additional ammonium hydroxide. The flask was charged with 0.5 g Darco KB, and 1.5 g Celite. The dark suspension was stirred at 20–25° C. for 1 hour. The suspension was filtered under reduced pressure through a bed of celite using a 5.5 cm Buchner funnel. The flask and filtercake were rinsed with 2×10 ml water.

A dark 1L one-neck, round-bottom flask equipped with a magnetic stirbar, addition funnel and nitrogen purge was charged with 375 ml acetic acid, and 10 ml 37% hydrochloric acid. Once the addition was complete, the pH of the mixture was adjusted to about less than or equal to 1 by the addition of 37% hydrochloric acid. The filtrate from the celite filtration step was charged to the addition funnel and added dropwise to the stirring acid solution over 30–45 minutes. Once the addition was complete, the pH was adjusted to about less than or equal to 1 by the addition of hydrochloric acid. The suspension was stirred at 20–25° C. for 1–2 hours; then filtered under reduced pressure using a 7 cm Buchner funnel. The filtercase was rinsed with 2×10 ml water.

A dark 500 ml, one-neck, round-bottom flask equipped with a stirbar, condenser, and nitrogen purge was charged with tin mesoporphyrin wetcake from the above step and 200 ml 1N HCl. The suspension, which ideally has a red color, was warmed to about 85–90° C. for 1–2 hours. The reaction was cooled to 20–25° C. and the suspension was filtered under reduced pressure using a 7 cm Buchner funnel. The filter cake was rinsed with 2×20 ml 0.1N HCl and dried at 85–90° C. for 24–48 hours. About 5 to 7 g of pharmaceutical grade pure tin mesoporphyrin chloride (tin (IV) mesoporphyrin IX dichloride) were obtained, for about a 50–70% yield, with a purity greater than or equal to 99%, as judged by HPLC analysis.

EXAMPLE 4

Representative large scale production of tin mesoporphyrin IX chloride (tin (IV) mesoporphyrin IX dichloride or stannsoporfin)

Step 1

A 200 L reaction vessel which has been pressure tested and inerted with nitrogen is charged with 0.6 kg of 5% palladium on carbon (50% water by weight). Without agitation, the vessel is charged with 6.0 kg hemin and 161.0 kg formic acid, while minimizing the exposure of the ingredients throughout this reaction to visible or ultraviolet light. The vessel is pressurized with hydrogen to 30–35 psi at 20–25° C. The reaction mixture is agitated vigorously for a minimum of 30 minutes and warmed to 85–90° C. With vigorous agitation, the reaction temperature is maintained at 85–90° C. with a hydrogen pressure of 45–55 psi for a period of 60–75 minutes. The reaction is then cooled to 45–50° C. while maintaining pressure and hydrogenation is continued for a further 6 hours. The reaction is cooled to 20–25° C. The reactor is depressurized and inerted (flushed) with nitrogen. The reactor is charged with a dispersion agent, such as 3.0 kg hyflo supercel, suspended in 36 kg formic acid. The reaction mixture is then filtered to remove the catalyst.

The filtercake is rinsed with 2×61 kg formic acid. 170 L of the filtrate is transferred to a 200 L reaction vessel and cooled to 10–15° C. The reaction mixture is distilled under a reduced pressure of 20–60 mmHg, with a maximum reactor temperature of 50° C., to a residual volume of 25–35 L. The reminder of the filtrate is transferred into the reactor and cooled to 10–15° C. The reaction mixture is distilled under a reduced pressure of 20–60 mmHg, with a maximum reactor temperature of 50° C., to a residual volume of 25–35 L. The temperature of the reactor is cooled to 20–25° C. To the reaction vessel is charged with 89.1 kg methyl tert-butyl ether over a minimum of 1 hour. Upon completion of the addition, the reaction is agitated at 20–25° C. for a minimum of 2 hours. The reaction mixture is cooled to −20 to −25° C. over a minimum of 1 hour. The reaction is agitated at −20 to −25° C. for a period of 4 hours. The suspension is filtered through a cotton terylene cloth at −20 to −25° C. The filtercake is rinsed with 2×6 kg methyl tert-butyl ether. The product is dried under vacuum with a maximum oven temperature of 55° C. until it passes drying specifications. Once dry, the product (mesoporphyrin IX formate) is packaged. The theoretical yield for this reaction is 6.1 kg. Typically, the product is isolated with a yield of 4.6–5.8 kg (75–95%).

Step 2

An inerted reaction vessel is charged with 5.3 kg tin (II) chloride, 1.1 kg ammonium acetate, and 45.3 kg acetic acid. The suspension is moderately agitated at 20–25° C. for a minimum period of 2 hours. An inerted 200 L reaction vessel is charged with 4.6 kg mesoporphyrin IX formate from step 1, and 45.0 kg acetic acid. The mesoporphyrin suspension is warmed to 45–55° C. with moderate agitation for a period of 2 hours. With moderate agitation, under nitrogen, the tin chloride suspension is transferred into the mesoporphyrin suspension while maintaining a temperature of 45–55° C. in the vessel. The transfer lines are rinsed with 5.9 kg acetic acid. With vigorous agitation, nitrogen and air are bubbled into the reaction at such a rate so as to maintain an oxygen level less than 2% within the reactor. This aeration is maintained throughout the reaction. With vigorous agitation, the reaction mixture is warmed to reflux (ca. 110° C.) for a minimum period of 3 hours.

The reaction is cooled to 60–70° C. and 45.8 kg purified (de-ionized) water is added over a minimum of 30 minutes. With moderate agitation, the reaction temperature is cooled to 20–25° C. over a minimum of 1 hour. The reaction mixture is agitated at 20–25° C. for a minimum of 1 hour. The product is filtered through a cotton terylene cloth and the filtercake rinsed with 2×9 kg purified water. The wet filtercake is transferred to a 200 L reaction vessel followed by 30.1 kg purified water, 4.6 kg 31% hydrochloric acid. The transfer lines are rinsed with 5 kg purified water. With moderate agitation, the suspension is warmed to 85–90° C. for a period of 1–3 hours. The reaction mixture is cooled to 20–25° C. and 31.0 kg acetone is added over a minimum period of 30 minutes. The suspension is agitated at 20–25° C. for a minimum of 1 hour. The product is filtered through a cotton terylene cloth and the filtercake rinsed with 2×6 kg acetone. The product is dried under a stream of nitrogen on the filter until it passes drying specifications. Once dry, the crude product (substantially pure (about or more than 95%) tin (IV) mesoporphyrin IX dichloride) is packaged. The theoretical yield for this reaction is 5.3 kg. Typically, the crude, substantially pure tin mesoporphyrin product is isolated with a yield of 4.0–4.8 kg (75–90% yield).

Step 3

An inerted 200 L reactor is charged with 1.8 kg crude, substantially pure tin mesoporphyrin, formed via Steps 1 and 2, and 31 kg WFI (water for injection) with moderate agitation at 20–25° C. The reactor is charged with 2.4 kg 28% ammonium hydroxide. The resultant solution is agitated at 20–25° C. for 30 minutes, prior to testing pH to ensure that it is greater than 9. If not, additional ammonium hydroxide is added in small portions until this pH level is achieved. To the resultant solution is charged 0.1 kg Darco KB activated carbon and 0.2 kg hyflo supercel suspended in 2.3 kg purified water. With moderate agitation, the suspension is agitated at 20–25° C. for a minimum of 30 minutes. The suspension is filtered through a sparkler filter to remove solids, leaving a filtrate. The filter cake is rinsed with 13 kg purified water. An inerted 200 L reactor is charged with 69.3 kg acetic acid and 3.1 kg 31% hydrochloric acid. With moderate agitation, under nitrogen while maintaining a temperature of 20–25° C. the filtrate is added to the acetic acid HCl solution over a minimum of 45 minutes. The resultant suspension is agitated for 15 minutes at 20–25° C. prior to testing the pH level to ensure that the final pH is about less than or equal to 1. If not, additional hydrochloric acid is added in small portions until this pH level is achieved. The suspension is then agitated at 20–25° C. for a minimum of 1 hour. The product is filtered through a cotton terylene cloth and the filter cake is rinsed with 2×5 kg purified water.

With moderate agitation, at 20–25° C., an inerted 200 L reactor is charged with 31 kg purified water and 2.4 kg 28% ammonium hydroxide. The solution is then recirculated through the filtercake in order to completely dissolve all wetcake. The resultant solution is agitated at 20–25° C. for 30 minutes, prior to testing pH to ensure that it is greater than 9. If not, additional ammonium hydroxide is added in small portions until this level is achieved. To the resultant solution is charged 0.1 kg Darco KB activated carbon and 0.2 kg hyflo supercel suspended in 2.3 kg purified water. With moderate agitation, the suspension is agitated at 20–25° C. for a minimum of 30 minutes. The suspension is filtered through a sparkler filter to remove solids, leaving a filtrate. The filter cake is rinsed with 13 kg purified water. An inerted 200 L reactor is charged with 69.3 kg acetic acid and 3.1 kg 31% hydrochloric acid. With moderate agitation, under nitrogen while maintaining a temperature of 20–25° C. the filtrate is added to the acetic acid HCl solution over a minimum of 45 minutes. The resultant suspension is agitated for 15 minutes at 20–25° C. prior to testing the pH level to ensure that the final pH is about less than or equal to 1. If not, additional hydrochloric acid is added in small portions until this pH level is achieved. The suspension is then agitated at 20–25° C. for a minimum of 1 hour. The product is filtered through a cotton terylene cloth and the filter cake is rinsed with 2×5 kg purified water.

With moderate agitation, at 20–25° C., an inerted 200 L reactor is charged with 31 kg purified water and 2.4 kg 28% ammonium hydroxide. The solution is then recirculated through the filtercake in order to completely dissolve all wetcake. The resultant solution is agitated at 20–25° C. for 30 minutes, prior to testing pH to ensure that it is greater than 9. If not, additional ammonium hydroxide is added in small portions until this level is achieved. To the resultant solution is charged 0.1 kg Darco KB activated carbon and 0.2 kg hyflo supercel suspended in 2.3 kg purified water. With moderate agitation, the suspension is agitated at 20–25° C. for a minimum of 30 minutes. The suspension is filtered through a sparkler filter to remove solids, leaving a filtrate. The filter cake is rinsed with 13 kg purified water. An inerted 200 L reactor is charged with 69.3 kg acetic acid and 3.1 kg 31% hydrochloric acid. With moderate agitation, under nitrogen while maintaining a temperature of 20–25° C. the filtrate is added to the acetic acid/HCl solution over a minimum of 45 minutes. The resultant suspension is agitated for 15 minutes at 20–25° C. prior to testing the pH level to ensure that the final pH is about less than or equal to 1. If not, additional hydrochloric acid is added in small portions until this pH level is achieved. The suspension is then agitated at 20–25° C. for a minimum of 1 hour.

The resulting product is filtered through a cotton terylene cloth and the filter cake is rinsed with 2×5 kg purified water and 2×4 kg acetone. The filter cake product is dried under vacuum with a maximum oven temperature of 100° C. until it passes drying specifications. Once dry, the pharmaceutical grade pure product (tin (IV) mesoporphyrin IX dichloride or stannsoporfin) is packaged and is of pharmaceutical grade quality, as verified by analytical HPLC technique. The theoretical yield for this reaction is 1.8 kg. Typically, the final product is isolated with a yield of 1.1–1.6 kg (60–90%) and is pharmaceutical grade pure (at least about or exceeding 97%).

While foregoing is directed to the preferred embodiment of the present invention, other and further embodiments of the invention may be devised without departing from the basic scope thereof, and the scope thereof is determined by the claims that follow.

What is claimed is:

1. A method of producing a metal mesoporphyrin halide comprising:
   isolating a mesoporphyrin formate in substantially pure solid form; and
   reacting the mesoporphyrin formate with insert metals to form the metal mesoporphyrin halide.

2. The method of claim 1, further comprising forming a mesoporphyrin formate.

3. The method of claim 2, further comprising catalytically hydrogenating hemin in the presence of an acid to form the mesoporphyrin formate.

4. The method of claim 3, wherein the step of catalytically hydrogenating the hemin occurs in two steps.

5. The method of claim 4, further comprising heating a mixture of hemin and a hydrogenation catalyst under pressure at a first temperature for a first period of time and subjecting the mixture to a second temperature under pressure for a second period of time.

6. The method of claim 5, wherein the first temperature is higher than the second temperature.

7. The method of claim 1, wherein metal mesoporphyrin halide is a tin mesoporphyrin halide.

8. The process of claim 6, further comprising:
   a) subjecting a reaction mixture of hemin and a hydrogenation catalyst in an acid to hydrogen pressure of about 30–60 psi and then raising the temperature to about 85–95 C. and maintaining the temperature within that range for a period of about 1–3 hours;
   b) subjecting the reaction mixture to a further hydrogen pressure of about 30–60 psi at a temperature range of about 45–50 C. for a period of about 3–6 hours; and
   c) recovering the formate salt of mesoporphyrin IX from the reaction mixture by precipitation of the mixture with a solvent.

9. The process of claim 3, wherein the acid is formic acid.

10. The process of claim 7, wherein the solvent is an ether.

11. The process of claim 10, wherein the solvent is methyl tert-butyl ether.

12. The process of claim 11, wherein the hydrogenation catalyst is palladium on carbon.

13. The method of claim 1, wherein the quantity of metal mesoporphyrin halide formed by the process exceeds 1 kg.

14. A formate salt of mesoporphyrin IX.

15. The formate salt of claim 14, wherein the purity is greater than or equal to about 97%.

16. A formate salt of mesoporphyrin IX produced according to the process of claim 1.

17. The formate salt of claim 16, wherein the purity is greater than or equal to about 97%.

18. A process of converting a formate salt of mesoporphyrin IX to a metal mesoporphyrin halide, which comprises:
   a) drying the formate salt of mesoporphyrin IX to obtain a mesoporphyrin IX formate;
   b) subjecting the mesoporphyrin IX formate to a chemical metal insertion process reaction with a metal halide compound in the presence of an oxidant under buffered, acidic reaction conditions; and
   c) recovering the metal mesoporphyrin halide from the reaction mixture.

19. The process of claim 18 further comprising purification of the recovered metal mesoporphyrin halide.

20. A process of purifying a metal mesoporphyrin halide, which comprises:
   a) dissolving the metal mesoporphyrin halide in an aqueous basic solution to obtain a dissolved metal mesoporphyrin halide;
   b) treating said dissolved metal mesoporphyrin halide with charcoal to obtain a treated metal mesoporphyrin halide;
   c) adding said treated metal mesoporphyrin halide to a first aqueous acid solution to obtain a precipitated metal mesoporphyrin halide;
   d) triturating said precipitated metal mesoporphyrin halide in a second aqueous acid solution at elevated temperature to obtain a substantially pure metal mesoporphyrin halide; and
   e) drying said substantially pure metal mesoporphyrin halide.

21. The process of claim 20, wherein the metal mesoporphyrin halide is tin (IV) mesoporphyrin IX chloride.

22. A method of producing stannsoporfin comprising:
   isolating mesoporphyrin formate in substantially pure, solid form; and
   reacting the mesoporphyrin formate with a tin insert metal to form stannsoporfin.

23. The method of claim 22, wherein the isolating includes subjecting hemin to catalytic hydrogenation in formic acid.

24. The method of claim 23, wherein the catalytic hydrogenation is performed in reactor pressurized with hydrogen.

25. The method of claim 24, wherein the catalytic hydrogenation is performed in two steps.

26. The method of claim 25, wherein the first step in the catalytic hydrogen involves heating a reaction mixture of hemin and a hydrogenation catalyst to a first temperature for a first period of time and lowering the reaction mixture to a second temperature for a second period of time.

27. The method of claim 26, wherein the pressure in the reaction vessel is between about 30 psi and 60 psi.

28. The method of claim 27, wherein the first temperature exceeds about 850° C.

29. The method of claim wherein 28, wherein the second temperature is below about 50 ° C.

30. The method of claim 29, further comprising recovering the reaction mixture in an organic solvent.

31. The method of claim 30, further comprising reacting the recovered reaction mixture with a metal halide.

32. The method of claim 31, wherein the reaction is performed under buffered, acid reaction conditions in the presence of an oxidant to form tin mesoporphyrin halide.

33. The method of claim 32, further comprising purifying the tin mesoporphyrin halide.

* * * * *